(12) United States Patent
Huiku

(10) Patent No.: US 7,553,286 B2
(45) Date of Patent: Jun. 30, 2009

(54) REAL-TIME MONITORING OF THE STATE OF THE AUTONOMOUS NERVOUS SYSTEM OF A PATIENT

(75) Inventor: Matti Huiku, Espoo (FI)

(73) Assignee: Instrumentarium Corporation, Helsinki (FI)

(*) Notice: Subject to any disclaimer, the term of this patent is extended or adjusted under 35 U.S.C. 154(b) by 476 days.

(21) Appl. No.: 10/954,040

(22) Filed: Sep. 29, 2004

(65) Prior Publication Data

US 2006/0074333 A1    Apr. 6, 2006

(51) Int. Cl.
    *A61B 5/00*      (2006.01)
(52) U.S. Cl. .................. 600/529; 600/483; 600/300
(58) Field of Classification Search .......... 600/513, 600/529, 300, 324, 346, 509, 544, 518, 483, 600/549, 587
    See application file for complete search history.

(56) References Cited

U.S. PATENT DOCUMENTS

| | | | | |
|---|---|---|---|---|
| 5,372,140 | A * | 12/1994 | Pomfrett | 600/513 |
| 5,560,370 | A * | 10/1996 | Verrier et al. | 600/518 |
| 5,830,148 | A * | 11/1998 | Inukai et al. | 600/481 |
| 5,906,208 | A * | 5/1999 | Ishikawa et al. | 128/898 |
| 5,964,713 | A * | 10/1999 | Nomura et al. | 600/549 |
| 6,105,015 | A * | 8/2000 | Nguyen et al. | 706/26 |
| 6,168,569 | B1 * | 1/2001 | McEwen et al. | 600/557 |
| 6,315,736 | B1 * | 11/2001 | Tsutsumi et al. | 600/500 |
| 6,356,775 | B1 * | 3/2002 | Kondo et al. | 600/346 |
| 6,363,270 | B1 * | 3/2002 | Colla et al. | 600/324 |
| 6,641,542 | B2 * | 11/2003 | Cho et al. | 600/529 |
| 6,751,499 | B2 * | 6/2004 | Lange et al. | 600/544 |
| 7,034,692 | B2 * | 4/2006 | Hickle | 340/573.1 |
| 7,062,326 | B2 * | 6/2006 | Huvelle et al. | 607/18 |
| 7,069,070 | B2 * | 6/2006 | Carlson et al. | 600/519 |
| 7,101,339 | B2 * | 9/2006 | Daum et al. | 600/529 |
| 7,162,294 | B2 * | 1/2007 | Rowlandson et al. | 600/513 |
| 7,190,995 | B2 * | 3/2007 | Chervin et al. | 600/544 |
| 7,215,994 | B2 * | 5/2007 | Huiku | 600/544 |
| 7,367,949 | B2 * | 5/2008 | Korhonen et al. | 600/483 |
| 7,460,901 | B2 * | 12/2008 | Kettunen et al. | 600/513 |
| 2004/0127804 | A1 | 7/2004 | Hatlesad et al. | |
| 2005/0240087 | A1 * | 10/2005 | Keenan et al. | 600/301 |
| 2007/0076935 | A1 * | 4/2007 | Jeung et al. | 382/128 |
| 2007/0118054 | A1 * | 5/2007 | Pinhas et al. | 600/587 |

FOREIGN PATENT DOCUMENTS

DE       101 51 797       5/2003

OTHER PUBLICATIONS

Extended European Search Report dated Jan. 16, 2006.

* cited by examiner

*Primary Examiner*—Robert L Nasser
(74) *Attorney, Agent, or Firm*—Andrus, Sceales, Starke & Sawall, LLP

(57) ABSTRACT

The invention relates to a method and arrangement for monitoring the state of the autonomous nervous system (ANS) of a patient. A first measurement signal is acquired from a patient, the first measurement signal representing a physiological signal measured from the patient. In order to enable real-time monitoring of the state of the ANS, a second measurement signal indicative of a respiration rhythm of the patient is acquired and at least one indicator signal is generated by means of the first and second measurement signals. The at least one indicator signal may then be used to obtain an indication of the state of the autonomous nervous system of the patient.

29 Claims, 7 Drawing Sheets

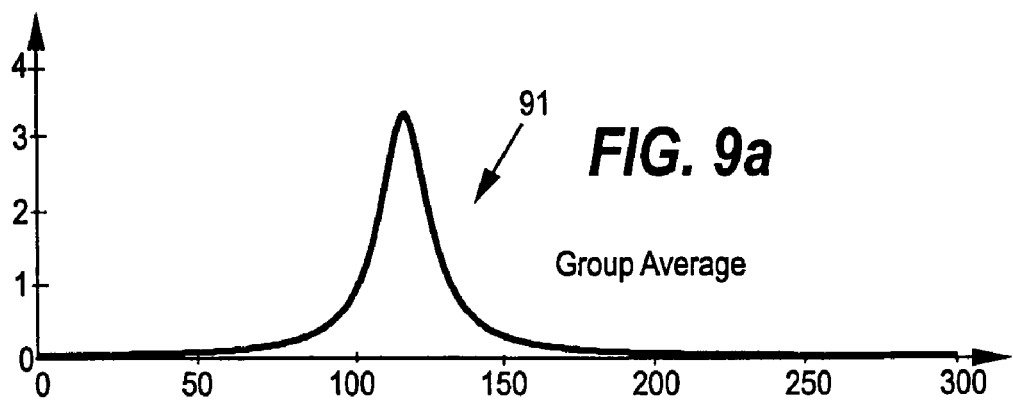
FIG. 9a Group Average
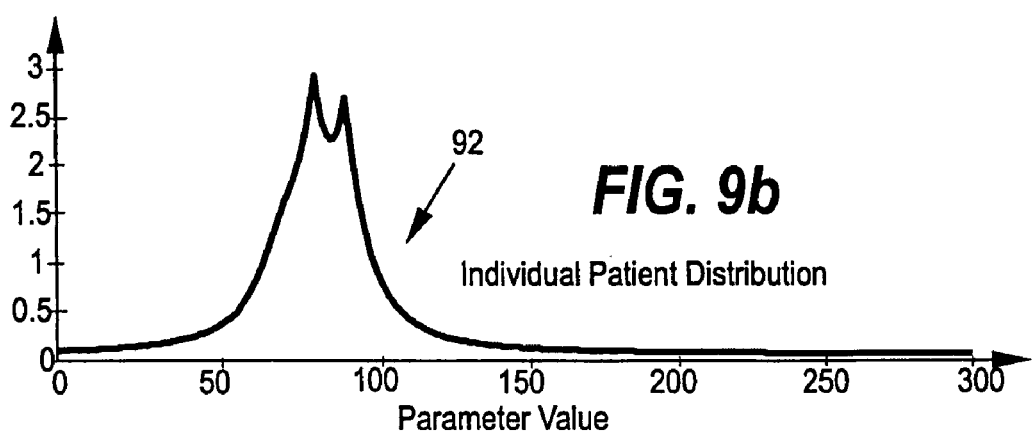
FIG. 9b Individual Patient Distribution
Parameter Value
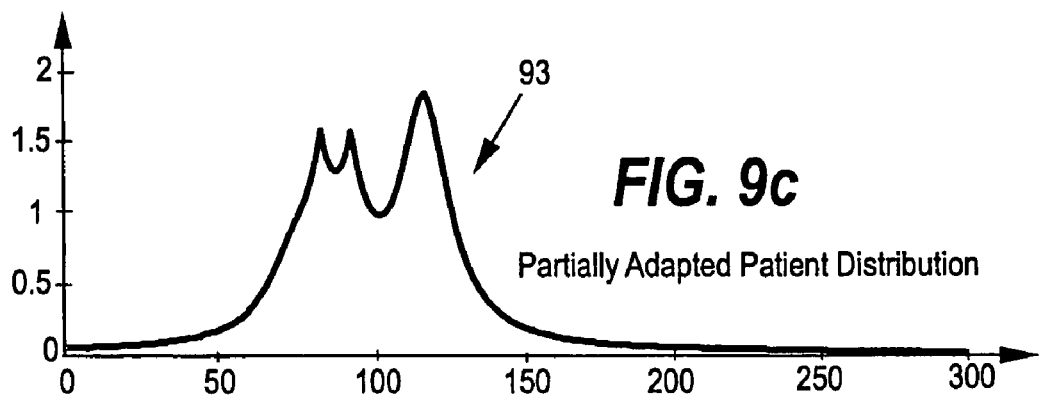
FIG. 9c Partially Adapted Patient Distribution
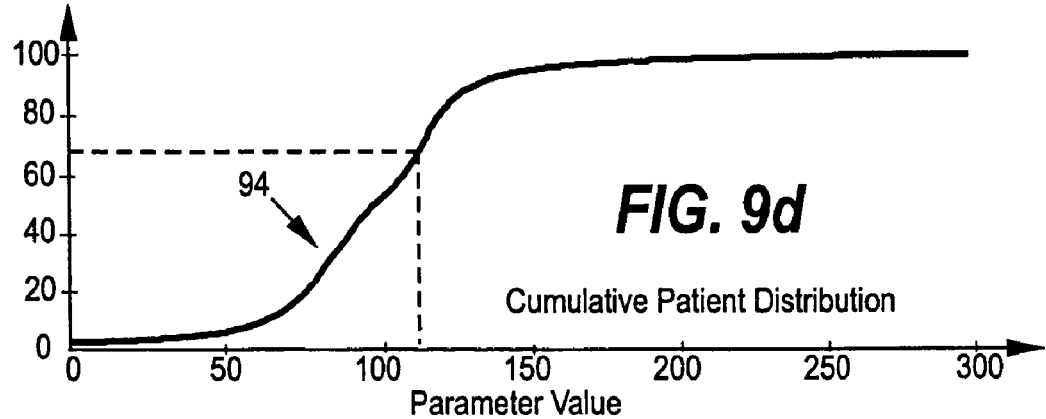
FIG. 9d Cumulative Patient Distribution
Parameter Value

US 7,553,286 B2

REAL-TIME MONITORING OF THE STATE OF THE AUTONOMOUS NERVOUS SYSTEM OF A PATIENT

FIELD OF THE INVENTION

The present invention relates generally to a method and arrangement for monitoring the state or activity of the autonomous nervous system (ANS) of a patient. As described below, the state of the ANS may be evaluated in various ways utilizing a physiological signal which is affected by the ANS through its regulation of various body functions. One example of such an evaluation process is the determination of the sympatho-vagal balance of a patient.

BACKGROUND OF THE INVENTION

Autonomic nervous system (ANS) is the 'unconscious' nervous system that controls and regulates virtually all of our basic body functions, such as cardiac function, blood circulation and glandural secretion. The main parts of the ANS are the parasympathetical and sympathetical nervous branches. The sympathetical nervous system usually prepares us for high stress situations by speeding up body functions, while the parasympathetical system restores, under conditions of normal ANS regulation, normal conditions in blood circulation by slowing down the heart rate (HR). The heart rate is mainly controlled by the parasympathetical vagal nerve. Pain, discomfort, and surgical stress may activate the sympathetical branch of the ANS and cause an increase in blood pressure, heart rate and adrenal secretion.

Sympathetical activation is often manifested in large low frequency (LF) variations in the heart rate, in blood pressure, and peripheral blood circulation. Vagal activation is mainly seen in heart rate, but also in blood pressure and circulation in high frequency (HF) band, in which modulations are usually largest. The HF component arises mainly due to respiratory influence. The sympatho-vagal balance is described by the LF/HF power ratio. This ratio is traditionally estimated in spectral domain. Fourier analysis is used to calculate the spectral power at fixed LF (below 0.15 Hz) and HF (from 0.15 to 0.4 Hz) frequency bands. The technique is well known in Heart Rate Variability (HRV) analysis.

Pain is an unpleasant sensory or emotional experience that is associated with actual or potential tissue damaging stimuli. It is always an individual and subjective sensation, which may be acute (nociceptive), elicited by noxious stimuli, or chronic pain that has outlived its usefulness to preserve tissue integrity. The perception of pain takes mainly place at cortex, and it may be suppressed in deep sedation and anesthesia by the general (global) inhibitory effects of sedative drugs and anesthetic agents. The responses to noxious stimulus may also be suppressed when the pain signal pathway is sufficiently suppressed at the subcortical level, often in the region of the brainstem and spinal cord. Both cortical and subcortical mechanisms play a role in pain management in modern surgical anesthesia or intensive care.

Analgesia refers to the absence of pain or loss of sensitivity to pain without unconsciousness in response to stimulation that would normally be painful.

When developing 'index type' numeric or other indicators reflecting the state of a patient, such as the activity of the ANS, the basic difficulty is to associate the index with a fixed scale in situations, in which the basic physiological parameters, such as the HR, measured from the patient do not have any 'normal' values, but vary over a wide range of values even in case of healthy patients. A special difficulty when evaluating the state of the ANS with the objective of getting an estimate of the adequacy of analgesia, for example, is the lack of an exact measure of the adequacy of analgesia, i.e. there is no quantity that can be directly related either to the adequacy of analgesia or to a specific drug (opioid) effect or body reflex. Furthermore, a change in a basic physiological parameter measured may indicate another physiological cause than the (in)adequacy of analgesia. In other words, the difficulty also lies in finding a measure that would be specific to the variable estimated, such as to the adequacy of analgesia.

Artificial ventilation of a patient shall often be considered as a stress factor for the patient. It can also generate artifacts in the signal, because the HF modulation may be excessively influenced by the resulting overpressure in the lungs and airways. In spontaneous (normal) breathing, this situation is seldom reached in such a degree. In normal breathing, the pressure and flow sensitive receptors in the atria of the heart and in the pulmonary and aortic vessels signal differently than in artificial overpressure ventilation. For example, the heart rate of a spontaneously breathing patient accelerates during inhalation and decelerates during exhalation, whereas the opposite occurs in overpressure ventilation. The ANS regulation of the blood circulation and heart rate is thus disturbed, which calls for special algorithms for estimating the sympathetical and parasympathetical activations and their balance.

As mentioned above, the sympatho-vagal balance is a well-known tool in HRV analysis for examining cardiovascular neural regulation. A general drawback related to the determination of the sympatho-vagal balance is that the current analysis method based on Fast Fourier Transform (FFT) is not suitable for real-time monitoring of a patient. This is due to the fact that a certain time, typically at least 1 to 2 minutes, is needed to obtain the frequency components of the signal. The main reason for the delay is the time needed to analyze the low frequency variations, i.e. the LF component of the signal, since several cycles are needed for the result.

Furthermore, the current analysis method is not suitable for patient monitoring systems requiring an analysis of non-stationary signals, such as noxious responses. Fast responses, i.e. responses with durations of about 10 to 15 sec, always cause non-stationarities in the signal. The FFT does not yield a reliable result in case of non-stationary signals including step-like changes in the signal values, and therefore the FFT should not be used for such signals.

The present invention seeks to alleviate or eliminate the above drawbacks and to bring about a mechanism that enables reliable real-time monitoring of the state or activity of the autonomous nervous system of a patient.

SUMMARY OF THE INVENTION

The invention seeks to provide a mechanism that allows real-time monitoring of the state of the autonomous nervous system of the patient. The present invention further seeks to provide a mechanism that yields a reliable result also when the physiological signal on which the monitoring is based is a non-stationary signal.

The present invention is based on the idea that the respiration originated modulation in the ANS activity may be used as a measure of the state of the ANS. In order to be able to distinguish the effects which disturb the operation of the ANS from the effects that do not carry any information about the state of the ANS, such as the effects caused by the mechanical operation of a respirator, a signal indicative of the respiration rhythm of the patient is generated and used to produce an indicator signal, which is based on a physiological signal measured from the patient. The indicator signal may be, for example, indicative of the irregularity of the respiration modulation in the physiological signal. If the respiration modulation is regular, i.e. if it repeats itself similarly from one respiration cycle to another, the ANS regulation is normal or not disturbed by external factors. However, the more there are irregularities in the respiration modulation, the more the operation of the ANS is disturbed by adverse factors, such as pain or discomfort.

Thus one aspect of the invention is providing a method for monitoring the state of the autonomous nervous system of a patient. The method includes acquiring a first measurement signal from a patient, the first measurement signal representing a physiological signal measured from the patient and obtaining a second measurement signal indicative of a respiration rhythm of the patient. The method further includes generating, based on the first and second measurement signals, at least one indicator signal for obtaining an indication of the state of the autonomous nervous system of the patient.

Another aspect of the invention is that of providing an arrangement for monitoring the state of the autonomous nervous system of a patient. In one embodiment, the arrangement includes a measurement device configured to acquire a first measurement signal from a patient, the first measurement signal representing a physiological signal measured from the patient, an input configured to receive a second measurement signal indicative of respiration rhythm of the patient, and a first controller configured to generate, by means of the first and second measurement signals, at least one indicator signal to obtain an indication of the state of the autonomous nervous system of the patient.

In a further embodiment, the invention provides a computer program embodied on a computer-readable medium for monitoring the state of the autonomous nervous system of a patient. The computer-readable program code comprises a first computer-readable program code portion for receiving first measurement signal data, the first measurement signal data representing a physiological signal measured from the patient, a second computer-readable program code portion for receiving second measurement signal data indicative of a respiration rhythm of the patient, and a third computer-readable program code portion for generating, by means of the first and second measurement signal data, at least one indicator signal for obtaining an indication of the state of the autonomous nervous system of the patient.

As disclosed below, the indicator signal may be determined in various ways, and the said signal may be utilized in various ways to obtain an indication of the state of the ANS of the patient. In one embodiment of the invention, the state of the ANS is estimated by calculating the sympatho-vagal balance of the patient, or a ratio similar to the sympatho-vagal balance. However, the solution of the invention may also be utilized for calculating other variables indicative of the state of the ANS of the patient, such as an index indicative of the adequacy of analgesia or an index indicative of the depth of anesthesia.

Using the technique of the invention, the result is obtained within a time period of only about one respiration cycle, which is normally between 5 and 10 sec. Furthermore, as the present invention is based on a time domain analysis of the physiological signal, it is not disturbed by the non-stationarities in the signal. A further advantage of the solution of the invention is that the modulation at the respiration frequency may have any waveform. In other words, the mechanism of the invention is also able to take into account waveforms different to sinusoidal waveforms.

Other features and advantages of the invention will become apparent by reference to the following detailed description and accompanying drawings.

BRIEF DESCRIPTION OF THE DRAWINGS

In the following, the invention and its preferred embodiments are described more closely with reference to the examples shown in FIGS. 1 to 13 in the appended drawings, wherein:

FIGS. 9a to 9d illustrate another embodiment of the normalization process of the invention;

DETAILED DESCRIPTION OF THE INVENTION

Figure 1:
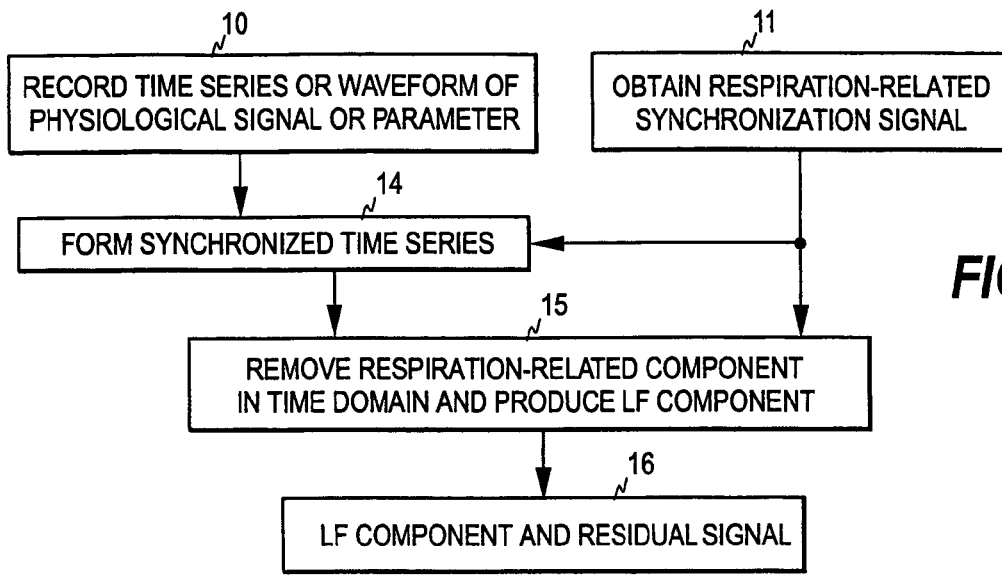
FIG. 1 is a flow diagram illustrating one embodiment of the invention.

FIG. 1 illustrates one embodiment of the present invention. For the actual measurement, signal data is first obtained from the patient. This may be implemented in a conventional manner, i.e. while the patient is connected to a patient monitoring system a physiological signal is recorded and stored in a memory of a monitoring device. The physiological signal may be, for example, an ECG waveform or a photoplethysmographic signal, a blood pressure signal or a signal representing a physiological trend parameter, such as heart rate, pulse rate, or blood pressure. However, as discussed below, the physiological signal is such that the respiration of the patient causes modulation to the signal.

The recorded signal data may then be pre-processed for extracting the parameters that are not directly available as a trend parameter, such as beat-to-beat or cycle-to-cycle intervals of the waveform. For example, to obtain an RRI signal the moments at which the R-peaks occur in the QRS-complex are extracted from an ECG waveform, and the R-to-R intervals are recorded. In case of a plethysmographic waveform, the pulse amplitude may be extracted for each pulse beat.

A time series is then formed from the values of the extracted signal. The above steps may thus be performed at step 10 shown in the figure. Below, the time series or waveform of the physiological signal or parameter thus obtained is termed the first measurement signal.

Simultaneously with the recording of the first measurement signal, a respiration-related measurement signal is obtained from the patient or from a respirator (step 11).

Below, this signal is termed the second measurement signal. The second measurement signal is indicative of the respiration rhythm of the patient.

In the embodiment of FIG. 1, the second measurement signal indicates the phase of the respiration rhythm of the patient, such as the start of each inspiration period. This signal may be obtained by any suitable means. If the patient is artificially ventilated, the second measurement signal may be obtained from the respirator or ventilator in question. If the patient is breathing normally, the respiration rhythm may be obtained from a strain-gauge transducer attached around the chest of the patient, for example. It is thus also to be noted here that in this context the term respiration covers both normal and artificial breathing.

The first measurement signal is then subjected to an interpolation step 14 where information about the phase of the respiration of the patient is attached to it. Each respiration cycle is divided into a fixed number of time slots and in step 14 the values of the first measurement signal at said time slots are defined. Step 14 thus outputs a time series in which the successive data points are synchronized with the respiration rhythm of the patient, i.e. for each respiration cycle of the patient a predetermined number of data points (signal values) are obtained at regular intervals, the said predetermined number being independent of the length of the respiration cycle or the number of heart beats within in the respiration cycle, for example.

A low frequency (LF) component is then separated from the synchronized time series in step 15 by first removing a periodic signal component having a period equal to the respiration cycle. As a result, the low frequency component and a residual signal (RS) are obtained (step 16). The residual signal includes a high frequency (HF) component and possibly also a fast beat-to-beat component, if the physiological signal is a heart rate related signal. The beat-to-beat component results from beat-to-beat variations in a heart rate related physiological signal. The HF component is also termed a respiration component, since it represents variations having substantially the same periodicity as the respiration. The LF and B2B component, respectively, represent variations slower and faster than the periodicity of the respiration.

Figure 2:
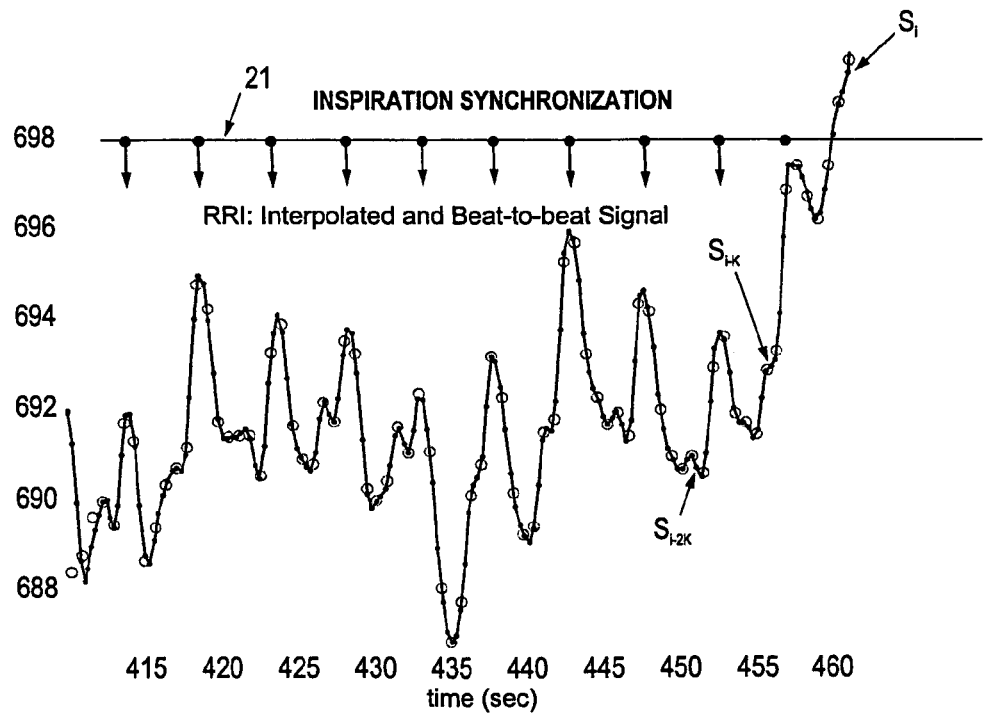
FIGS. 2 and 3 illustrate an example of the extraction of the low frequency component of the physiological signal or parameter in the embodiment of FIG. 1.
Figure 3:
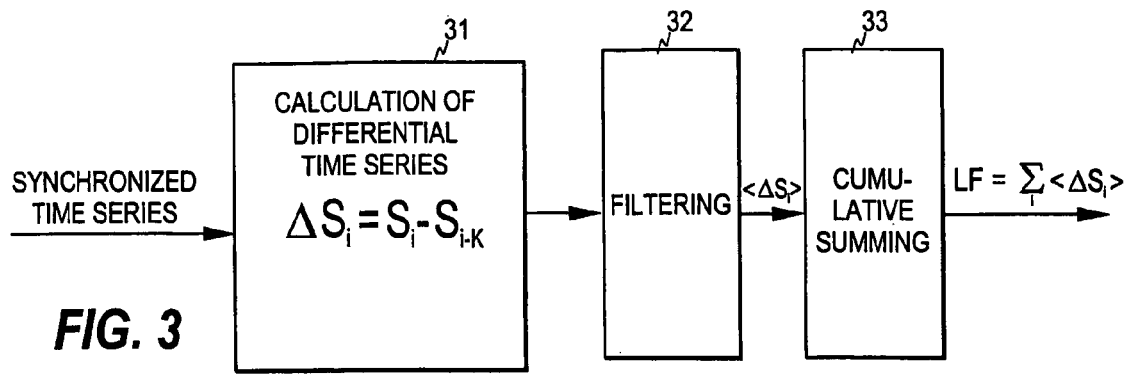

FIGS. 2 and 3 illustrate one embodiment of the calculation performed in step 15. FIG. 2 is a time line showing a synchronized time series 20 obtained from step 14 and the synchronization signal 21 obtained from step 11. The synchronization signal indicates the start of each respiration cycle, the start moments being denoted by downward arrows in the figure. It is assumed here that each respiration cycle includes K=16 interpolated signal values (data points) $S_i$, where the subscript i is the sequence number of the data point in the time series. Typically, one respiration cycle is about 6 seconds in duration and it thus normally contains 6 to 8 heart beats. A signal value is normally obtained for each heart beat. In step 15, the number of signal values is increased so that K signal values are obtained at even intervals for each respiration cycle. This is implemented by interpolating new values by means of the values measured during one respiration cycle. The first interpolated signal value in the respiration cycle is always at a certain moment of the synchronization signal.

FIG. 3 illustrates the three sub-steps performed at step 15. First, a differential time series is formed at sub-step 31, each differential value representing the difference of the data point values obtained at the same phase of the respiration cycle but in successive respiration cycles. Sub-step 31 illustrates the formation of the difference time series assuming that the sequence number of the current data point is i. For the current data point $S_i$ a differential value $\Delta S_i = S_i - S_{i-K}$ is calculated, i.e. the current value of the differential time series is obtained by detracting from the current signal value the signal value obtained exactly one respiration cycle earlier. This differential value is calculated for each data point in the synchronized time series.

The physiological signal is thus divided into successive parts according to the respiration rhythm of the patient and K difference values are calculated for each respiration cycle (here, K=16).

The sum of the difference values is indicative of the low frequency variation in the measurement signal. However, before the summing operation, the difference values obtained are supplied to a filtering sub-step 32, where the values are filtered by means of an averaging filter, which may be a FIR or an IIR filter, for example. By means of the filtering the B2B variability may be removed from the difference signal $\Delta S_i$. In one embodiment, the filter calculates an average of the difference values obtained during K latest data points and yields an average difference $<\Delta S_i>$ for each data point. Typically, the average difference $<\Delta S_i>$ for each data point equals to one-$K^{th}$ of the sum of the difference values calculated over K latest data points. In another embodiment, the filter is a more effective high order FIR or IIR filter.

The difference signal does not any more contain a signal component at the respiration frequency, as this component is removed in the differentiation process. The spectral content of time series $\Delta S_i$ has thus a gap at the respiration frequency, which makes it easy to adjust the cutoff frequency of the filter in such a way that the LF band and the B2B band of the difference signal maintain correct shape in time domain. The filter may be a low-pass or a high-pass filter. If the filter is of a low-pass type, the filtering step removes the B2B component, whereas if the filter is of a high-pass type it removes the LF component. The LF component is thus obtained by filtering out the B2B component from the difference signal and by summing (i.e. integrating) the remaining difference signal to the LF signal, as illustrated in sub-step 33. This may be performed as the sum is a zero average signal.

The residual signal may then be obtained by subtracting the LF component from the original measurement signal. If an averaging or FIR filter is used in the step 15, the group delay of the filter shall be compensated before the subtracting step. The residual signal is below termed the first residual signal to distinguish it from the residual signals produced in further embodiments of the invention.

By means of the above method, in which the measurement signal is delayed by one respiration cycle and the delayed signal is subtracted from the original measurement signal (resulting in the difference signal), a signal component at the respiration rate is thus removed from the signal. As obvious from the above, if the respiration modulation is completely regular, i.e. if it repeats itself in a precise similar way from one respiration cycle to another, the LF component is a zero signal. However, if the respiration modulation that appears in the physiological signal is irregular, the irregularity appears in both the LF and B2B components. The LF and B2B components are thus indicative of the irregularity of the respiration modulation. These signals serve as the indicator signal mentioned above.

The above-described synchronous separation of the LF component in time domain may also be described as follows:

Extraction of the LF component:
Extract the time moments corresponding to the start of inspiration. The time moments may be detected based on an airway pressure or airway flow signal, for example.

Interpolate the original time series between the latest and the next latest inspiration time moments into K element regular interval array p_n; where n indicates the ordinality of the respiration cycle of the interpolated time series.

Make a signal p by concatenating p_n with earlier calculated p_n-1.

Calculate a K element offset differential signal d_n(i)=p(i)-p(i-K) for each i in p_n, where i indicates the data point in the interpolated time series.

Low pass filter d_n to form D_n. This step corresponds to step 32 in FIG. 3.

Integrate D_n for LF (LF(i)=LF(i-1)+D_n(i)). This step corresponds to the cumulative summing discussed at step 33 of FIG. 3.

Extraction of the HF and B2B components

Subtract the LF component from the original measurement signal to obtain the first residual signal.

One advantage of the invention is that the amount of buffered data may be kept low. Due to the sliding calculation of the LF component only K+1 latest data points need to be kept in memory.

Figure 4:
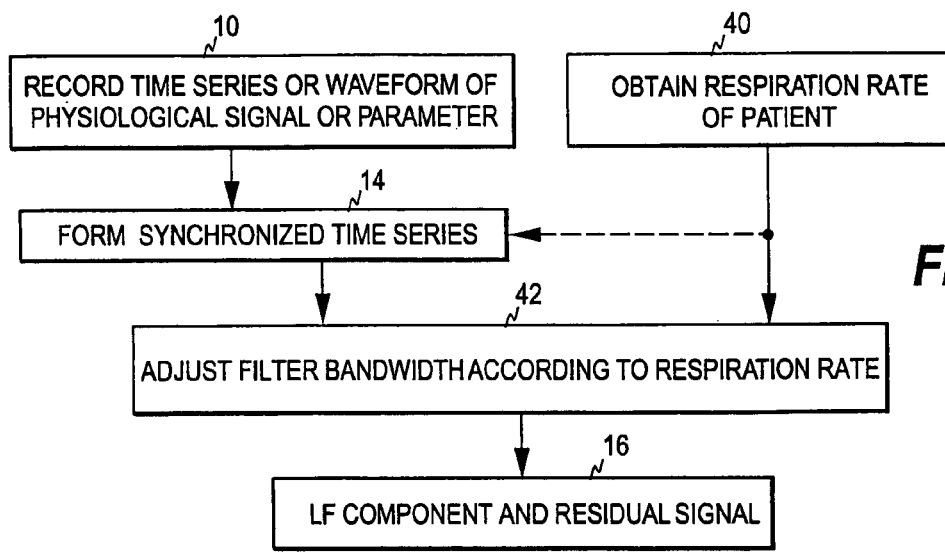
FIG. 4 illustrates an alternative embodiment for the extraction of the low frequency component.

Above, the LF component was separated from the original physiological signal in time domain by forming a time series phase-locked to the respiration rhythm of the patient. However, the signal indicative of the respiration rhythm of the patient does not necessarily have to carry phase information. FIG. 4 illustrates an alternative embodiment in which the LF component is separated by means of a filter controlled by the respiration rate of the patient. In step 40, the respiration rate of the patient is measured. The value of the respiration rate is then utilized to control the cut-off frequency of a FIR filter in step 42. In this embodiment, it is not necessary to form an interpolated time series. However, the respiration rate may be supplied to step 14 to form a time series including K values for each respiration cycle. The filter may be a low-pass filter or a high-pass filter, depending on whether the LF component or the beat-to-beat component is separated from the signal. The output signal of the filter serves as the indicator signal.

The LF component and the residual signal may then be used to calculate the sympatho-vagal balance indicative of the state of the ANS of the patient. In one embodiment of the invention, this is performed by dividing the power of the LF component by the power of the residual signal. This method corresponds to the traditional method based on a Fourier transform. However, the first residual signal, including the respiration (i.e. HF) and the B2B components, may also be processed further for calculating an indicator similar to the sympatho-vagal balance, i.e. a variable representing a ratio of the power of the sympathetical activation to the power of a signal component representing regular respiration modulation. This is discussed below.

In one embodiment of the invention, the accuracy of the method may be enhanced by removing the periodic signal component corresponding to second harmonic frequency of the respiration rate in the same way as the component at the respiration rate was removed above. The component at the second harmonic frequency may be removed by using a delay of K/2 data points. In this embodiment of the invention, the first residual signal is thus delayed by one half of the respiration cycle and the delayed residual signal is subtracted from the original first residual signal to obtain a new difference time series. The new difference time series is then filtered by an averaging filter and the filtered values are summed to obtain an LF component of the first residual signal. A second residual signal, i.e. a residual signal from which the second harmonic has been removed, is then obtained by subtracting this LF component from the first residual signal. In this embodiment, the final LF component is the sum of the two LF components calculated.

In a still further embodiment of the invention the accuracy of the method may be further enhanced by repeating the above steps once again to remove the third harmonic from the second residual signal.

In the above-described manner the accuracy of the method may be enhanced by removing one harmonic component at a time from the residual signal. The sympatho-vagal balance may then be calculated as described above using the final LF component and the residual signal from which the harmonic component(s) has/have been removed.

After the LF component has been extracted in time domain utilizing a signal indicative of the respiration rhythm of the patient, the remaining residual signal does not include any major non-stationarities (as these are in the LF component). Therefore, conventional filtering and signal processing techniques including Fourier and wavelet analysis may be used to separate the HF and the B2B components from the residual signal. Because the residual signal is a relatively high frequency signal, these techniques do not considerably slow down the analysis any more, as the analysis may be performed in 2 to 3 respiration periods, i.e. in less than 20 seconds instead of the 2 to 3 LF periods (about 2 to 3 minutes) required in the traditional method.

A further method for separating the HF and the B2B components from the residual signal is to utilize a FIR filter, which is controlled by the heart rate of the patient, i.e. the heart rate is used to control the bandwidth of the filter similarly as the respiration rate was utilized above.

When the residual signal has been divided into the HF and the B2B components, an indicator similar to the sympatho-vagal balance may be calculated by calculating the sum of the power of the LF and B2B components and dividing the sum by the power of the HF component.

Above, the residual signal RS was divided into the HF and B2B components using conventional spectral techniques. However, it is not necessary to perform the division of the residual signal in frequency domain. In a further embodiment of the invention, the residual signal RS is divided into a regular component $RS_{reg}$ which is substantially constant from one respiration cycle to another and to an irregular component $RS_{irreg}$ which varies from one respiration cycle to another. The regular component may be determined by calculating an average of the residual signal over a certain number of respiration cycles, such as ten. The irregular component is then obtained by subtracting the regular component from the signal values of the latest respiration cycle, i.e. $RS_{irreg}=RS_j-<RS>$, where j is the sequence number of the latest respiration cycle and <RS> is the average calculated. The irregular component $S_{irreg}$ of the entire signal is the sum of the LF component and the irregular component of the residual signal, i.e. $S_{irreg}=RSi_{reg}+LF$, and the regular component of the entire signal corresponds to the regular component of the residual signal, i.e. $S_{reg}=<RS>$. An indicator similar to the sympatho-vagal balance is then calculated by dividing the power of the irregular component by the power of the regular component. The calculated power ratio indicates the state of the ANS, as it represents the ratio of the power of the sympathetical activation to the power of the regular respiration component.

Another elegant technique for the analysis of the residual signal is to utilize the Walsh-Hadamard (W-H) transformation in one respiration cycle. A K*K Walsh-Hadamard matrix is first constructed and then the residual signal is divided into the components in the W-H base. The projection of the residual signal on the first W-H base vector is the constant offset component. The projections on the $2^{nd}, 3^{rd} \ldots 8^{th}$ base vectors describe the $2^{nd}$ and higher harmonics of the residual signal. The basic respiration modulation is projected on the $9^{th}$ to $16^{th}$ base vectors. The indicator indicative of the state of the ANS is then calculated by means of a regular component that remains constant from one respiration cycle to another and an irregular component that varies from one respiration cycle to another. In order to obtain the regular respiration component, the W-H coefficients are averaged over a certain number of respiration cycles, such as ten, and the power of the averaged coefficients is calculated. The power of the irregular component may be calculated, for example, as the Standard Deviation (SD) of the H-W coefficients over the same period. Finally, the total power of the LF and irregular components is divided by the power of the regular component in order to the get the indicator indicative of the state of the ANS.

The irregularity-regularity modulation ratio inside the respiration cycle may also be calculated without any transformation. In this case the residual signals are averaged directly cycle-by-cycle, the deviation of the residual signal values in one cycle is calculated, and finally the SD is calculated for the averaged signal (regular part) and for the deviation signal (irregular part). These are then rationed to get the irregularity-regularity ratio for the residual signal.

In another embodiment of the invention, the signal indicative of the irregularity of the respiration modulation in the physiological signal is calculated by means of correlation. In this embodiment, the time series phase-locked to the synchronization signal is formed as described in steps 10, 11, and 14 of FIG. 1. However, instead of forming one or more LF components, a correlation is calculated between the first measurement signal and a copy of the first measurement signal delayed by one or more respiration cycles. The correlation may also be calculated for only the first residual signal after removing the LF component, in which case the correlation describes the irregularities within one respiration cycle only.

Figure 5:
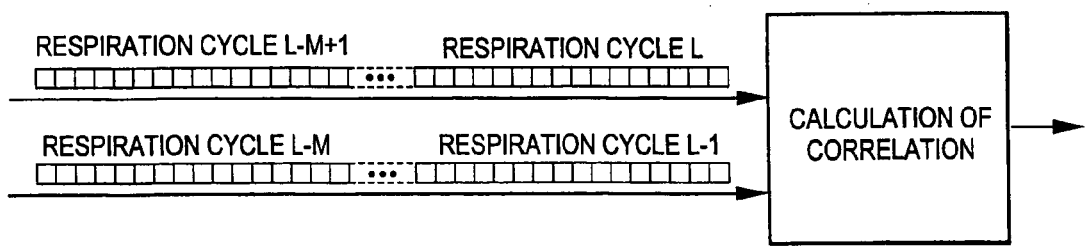
FIG. 5 illustrates one embodiment for generating a signal indicative of the irregularity of the respiration modulation.

One embodiment of the calculation of the correlation is illustrated in FIG. 5. In this embodiment, a predetermined number M of respiration cycles, such as ten, are taken from both the original and the delayed first measurement signal. If the index of the current respiration cycle is L, for example, the correlation is calculated between the original first measurement signal containing the data points of the respiration cycles whose indices are from L−M+1 to L and the delayed first measurement signal containing the data points of the respiration cycles whose indices are from L−M to L−1, where M is the said predetermined number, such as ten.

The correlation may be calculated slidingly for each data point, i.e. the calculation may be started at any phase of the respiration cycle. Furthermore, although the number of data points in the signals to be correlated is the same, this number does not have to be a multiple of the number of data points in one respiration cycle.

If the correlation is high, i.e. if the signal is regular, the ANS regulation is normal or near to normal. However, a lower correlation is indicative of disturbances in the activity of the ANS. The correlation thus serves as the indicator signal mentioned above. The correlation may also be used to calculate an index indicative of the adequacy of analgesia or an index indicative of the depth of anesthesia, for example.

In a further embodiment of the invention, the signal indicative of the irregularity of the respiration modulation in the physiological signal is calculated based on the difference values $\Delta S_i$ discussed in connection with FIGS. 2 and 3. Instead of calculating the LF component or the correlation, a variance is calculated for N latest difference values obtained. The number of difference values used for the calculation may vary and the number does not have to be a multiple of the number of data points in one respiration cycle. Such as the correlation, the variance calculated for the difference values is indicative of the irregularity of the respiration modulation; the higher the variance the higher the degree of irregularity. Thus the variance is also indicative of the state of the ANS of the patient and serves as the indicator signal. The calculated variance may then be used to calculate an index indicative of the adequacy of analgesia or an index indicative of the depth of anesthesia, for example. Similarly as in the embodiments based on the determination of correlation, the variance may also be calculated based on entire signal or the (first) residual signal.

Figure 6:
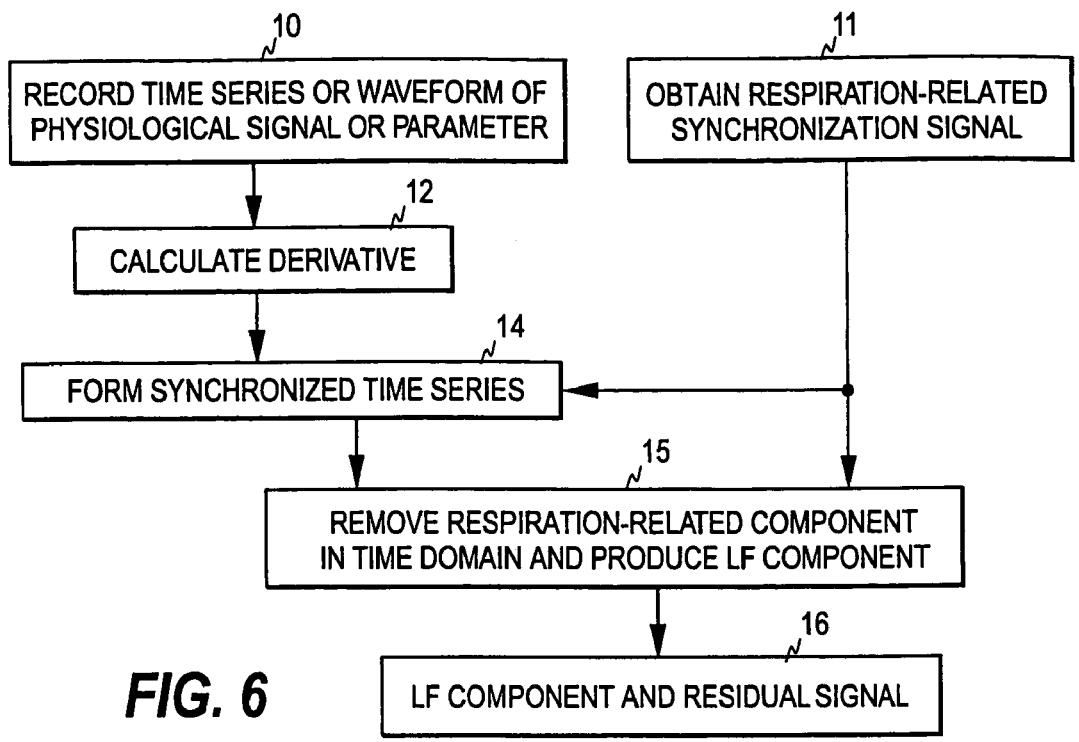
FIGS. 6 and 7 are flow diagrams illustrating, respectively, two further embodiments of the invention.

The control in the ANS branches is mediated by a mechanism of continuous firing of the nerve branches. For example, the balance between vasoconstriction and vasodilation is maintained by about 1 Hz firing of the sympathetical blood vessel smooth muscle nerve, less firing meaning vasodilation and more firing vasoconstriction. In the same way, the baroreflex is mediated (vagally) through more intense firing during high blood pressure and less firing during low pressure. In anesthesia, the nerve traffic is suppressed, but still the same principle of the control is maintained. However, sympathetical firing is often burst-type, leading to a sudden change (a kind of arousal) in the physiological parameter. This kind of sympathetical change is enhanced, if the original physiological signal or parameter is first derivated, and only then analyzed in more details. Peripheral blood circulation, for example, is sympathetically controlled, and, therefore, it is advantageous to first derivate the first measurement signal for better and more specific results. FIG. 6 illustrates an embodiment of the invention in which the derivative of the physiological signal is used. In this embodiment, the first measurement signal is thus derivated at step 12 prior to the formation of the synchronized time series, i.e. in this embodiment the synchronized time series 20 of FIG. 2 consists of successive values of the derivated signal. Other steps of the method may be performed as discussed in connection with the embodiment of FIG. 1. Generally, all the above embodiments discussed in connection with FIGS. 1 to 5 may also be used in connection with the embodiment utilizing the derivative of the physiological signal.

The derivation of the signal suppresses very slow variations in the signal. These often originate from slow ANS regulation mechanisms, such as temperature regulation, which are not good measures for surgical stress or antinociception, for example.

Another advantage of the derivation relates to elimination of the adverse effects of a mechanical ventilator on parameter variability. The signal, such as PPG amplitude or RRI interval, is often modulated by mechanical effects of the overpressure ventilation. The 'gain' of the autonomic regulation is nearly of 1/f-nature, meaning that the lower the ventilator rate, the larger the modulation of the RRI interval or the PPG amplitude. The consequence from the nearly 1/f Fourier spectrum is that the derivated Fourier spectrum is almost flat. When the respiration rate is changed, the derivated parameter remains unaffected by the change, although the original parameter obeys the 1/f-gain amplification. Time derivated measurement signal is thus less sensitive to the ventilator settings. Furthermore, since the LF and HF components are not sensitive to external mechanical effects, they are more specific to noxious responses.

Figure 7:
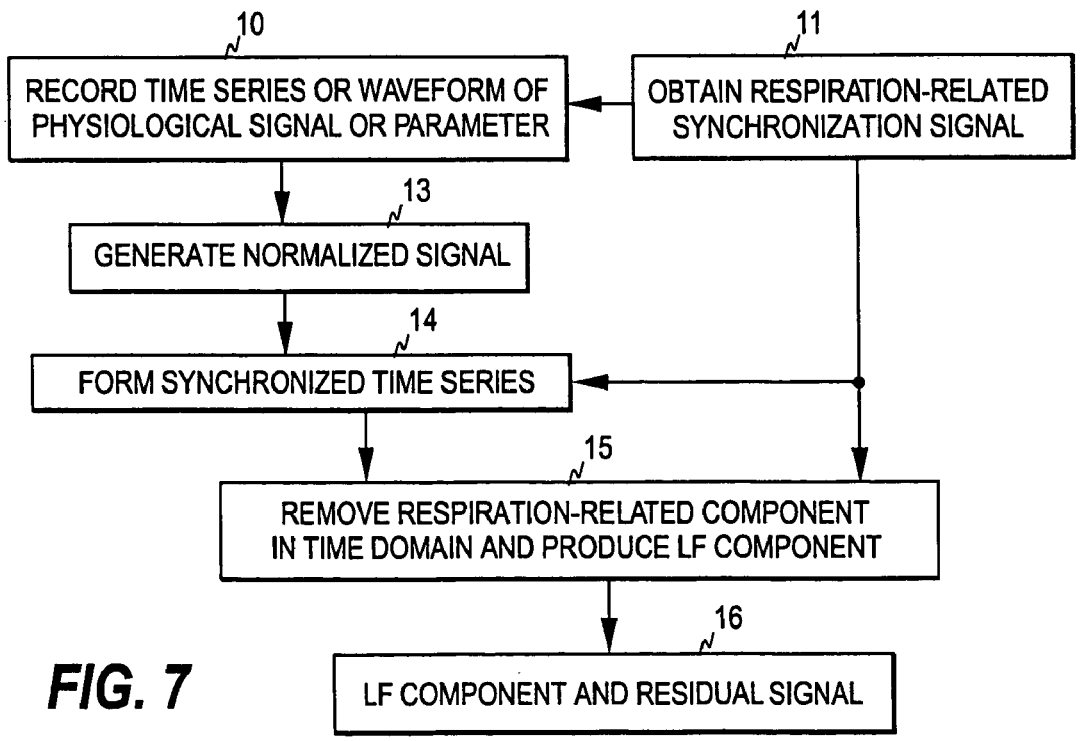

In another embodiment of the invention, a normalization process is performed in which the measurement signal is converted into a normalized signal, i.e. to a signal that has a predetermined value range and predetermined distribution characteristics for all patients. The normalization process thus "forces" the values of the measurement signal to a certain value range regardless of the values of the input signal. FIG. 7 illustrates an embodiment of the invention in which the normalization process is utilized. In this embodiment, the first measurement signal is thus normalized at step 13 prior to the formation of the synchronized time series, i.e. in this embodiment the synchronized time series 20 of FIG. 2 consists of successive values of the normalized measurement signal. Other steps of the process may be performed, for example, as discussed in connection with the embodiment of FIG. 1. However, normalization may also be used in connection with the other embodiments of the invention, such as the embodiment of FIG. 4.

In step 13, the original measurement signal may be transformed into a Gaussian signal with constant mean and constant variance or to a signal with even (linear) distribution of signal values. Usually the transformation performed yields a zero mean normal distribution with a constant standard deviation over a certain time range. The measurement signal is transformed into the same Gaussian or linear statistics for all patients, which allows patient-to-patient comparisons. The normalization may be performed by means of a histogram transformation, which conserves the frequencies and fractal properties of the original time series, but which may distort the amplitudes, depending on the output distribution of the transformation. The transformation thus provides various possibilities to enhance certain changes and to make these changes comparable between individual patients. For example, the transformation may be such that when the modulation is HF dominated, the LF/HF ratio is smaller than without normalization, whereas the contrary is true for LF dominated signals. One advantage of the transformation is in situations in which the LF modulation (i.e. sympathetical feature) is extracted from one physiological signal or parameter, such as PPG, and the HF modulation (i.e. parasympathetical feature) from another signal or parameter, such as the HR. In addition to that all patients have the same absolute parameter values, all parameters may also be normalized to the same common scale. Because a PPG signal is mainly sympathetically controlled and an RRI signal is mainly parasympathetically controlled, a better sympatho-vagal balance may be calculated by using an LF component from a PPG signal and an HF component from an RRI signal. Cross-parameter variables thus become possible, because after the histogram transformation all parameters are in the same units. The histogram transformation is also optimal in situations, in which the desired end-results, such as different indices of analgesia or anesthesia, shall be normalized into a fixed range. In one embodiment of the invention, the histogram transformation may be utilized to map any such index, for example an index varying non-linearly between −20 and 5, into a constant linear value range, such as from zero to one hundred.

Anesthetic agents suppress both cortical and subcortical activities. Therefore, hypnotic agents, for instance propofol, decrease the level of both the sympathetical and parasympathetic activity. When there is a need to estimate surgical stress or antinociception in a patient, the estimation method shall be insensitive to the general neuronal inhibitory effects of these agents. The estimation of the sympatho-vagal balance meets these requirements, as the ratio is unaffected by the general suppression in the neuronal activity. One method which is particularly suitable for estimating the sympatho-vagal balance is to scale (i.e. normalize) the signals to the same total power. After such normalization, which may be made using a histogram transformation, the estimation of only either the sympathetical or parasympathetical feature is enough to estimate the balance between these. In other words, when normalization is used, an estimate of the state of the ANS may be obtained by calculating only one of the LF and HF components.

The histogram transformation may be, for example, such that it normalizes the output signal to a preset Gaussian data value distribution over a time window of 3 to 5 minutes, for example. The variance (i.e. the total power of the LF and HF components) of the signal is then constant in this window. Both the HF and the LF component contribute to this total power. A shift towards LF dominance correspondingly decreases the HF power. Now, the sympatho-vagal ratio may be measured by measuring only one of the signal components, for example the LF component. This is advantageous especially when artificial ventilation of the patient blocks the normal ANS regulation seen in the HF component. (The HF component is contaminated by the ventilatory effects.) The Gaussian normalization followed by LF power measurement results in a better estimate of the sympatho-vagal ratio, especially if the derivation of the signal is used for eliminating the ventilatory effects.

Figure 8:
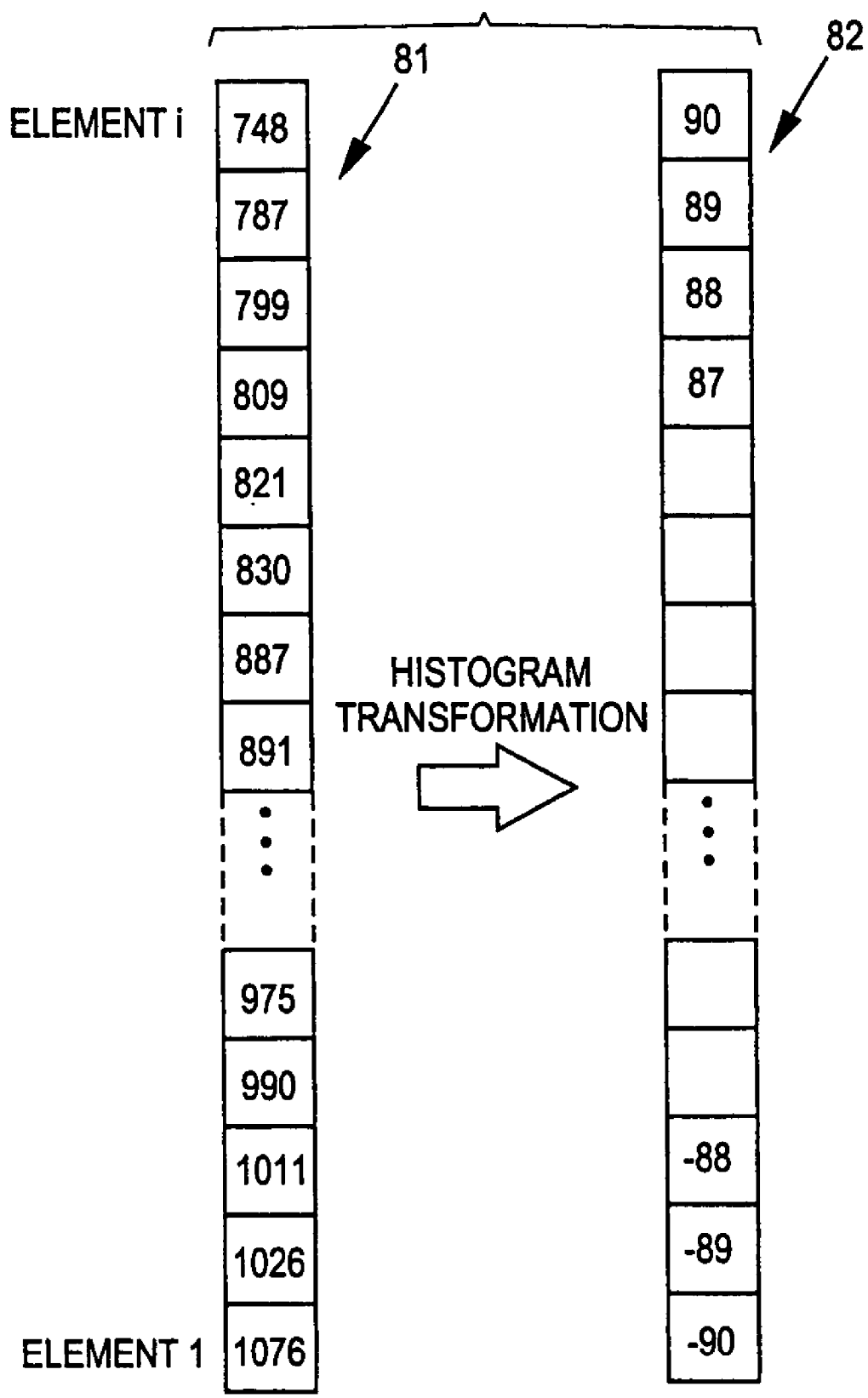
FIG. 8 illustrates one embodiment of the normalization process according to the invention.

The normalization may be performed by means of a histogram transformation, which is illustrated in FIG. 8. In the histogram transformation, an input array 81 and an output array 82 are formed. The input array (buffer) comprises i input elements, also termed bins, storing, respectively, i input values sorted in ascending or descending order, while the output array (buffer) comprises fixed index values sorted in ascending or descending order and stored in i output elements. In the example of FIG. 8, the index values of the output buffer range from −90 to +90 corresponding to the total number of values in the input buffer, i.e. i=181 (typically 3 minutes of RRI or PPG data). The signal values obtained from the pre-processing phase are forced to the value range of the output buffer. This may be implemented in three different ways depending on whether full adaptation, partial adaptation, or no adaptation to the incoming signal is utilized. All adaptation schemes preserve the frequency and fractal properties of the original signal, and therefore, the normalization does not influence the calculation of the sympatho-vagal ratios, i.e. the relative powers at the LF and HF bands or the regularity-irregularity analysis over certain time range. These embodiments of the histogram transformation are discussed in the following.

In full adaptation, the latest signal values of the measurement signal are stored in the input array so that the value of each new data point replaces the oldest value in the input array. When a new value is obtained, the oldest value in the input array is deleted, and the remaining values and the new value are sorted to form a new input array. The output value of the transformation is then obtained by means of the output array as the index value that corresponds to the location of the new value in the input array. In other words, if the new value is stored in the $k^{th}$ ($k \leq i$) element in the sorted input array, the output value is the index value stored in the $k^{th}$ element of the output array. FIG. 8 shows the R-to-R intervals (RRIs) obtained from an ECG signal, each RRI value indicating the time interval in milliseconds between two consecutive R-peaks of an ECG signal. If full adaptation is utilized, the value of each new data point obtained from the original RRI signal thus replaces the oldest value in the input array. In this way, the level of the signal may change but the output values remain between the lowest and highest indices. The time series obtained from the output array 82 may thus be such that the mean value is constant and the variability of the parameter is limited to a certain range and certain distribution around the mean value. As mentioned above, for example a Gaussian or even distribution with zero mean value may be used for the values output from the transformation.

In case no adaptation to the incoming signal is used in the transformation, the input array remains the same regardless of the incoming signal values. The input array may be formed based on values measured from a large patient group, which yields a wider distribution of input values. Thus, instead of storing the latest i values of the same patient, the input array may store i fixed values representing the distribution of the values of the measurement signal among a (large) group of patients. When a new value of the measurement signal is obtained, the output value of the transformation is obtained in the above-described manner as the index value that corresponds to the location of the new value in the sorted input array.

Partial adaptation to the incoming signal refers to the combination of the above two methods. For example, in the partial adaptation two input arrays may be used, one adapting fully to the incoming signal and the other being a fixed array storing values measured from a group of patients. Based on the two input arrays, a combined input array may be formed. When a new value is obtained from the pre-processing phase, the output value of the transformation is then obtained by means of the output array as the index value that corresponds to the location of the new value in the combined input array. The combined input array may be formed in various ways. For example, the two input arrays may have the same length as the output array and the values of the combined input array may be obtained by first sorting the input values and then downsampling them by taking only every second element to the combined input array. The summed length of two input arrays may also correspond to the length of the output array, in which case the combined input array may be obtained simply by taking the values of both input arrays and sorting them in desired order. For example, the length of each input array may be i elements, if the length of the output array is 2i elements. One input array may then include i reference values obtained from a large patient group, the values having even intervals, for example, while the other input array may includes i latest values of the incoming first measurement signal. The values of the two input arrays are then sorted, for each new value of the incoming signal, in descending or ascending order to obtain the combined input array that indicates the index value corresponding to the current value of the incoming signal.

A further preferred embodiment of the partial adaptation is illustrated in FIGS. 9a to 9d. FIG. 9a illustrates a parameter distribution curve 91 for a large number of patients representing a certain patient group in general anesthesia. The size of the patient group may be very large representing about 1000 patients, for example. The range of the parameter values, in the figures from 0 to 300, is advantageously selected to be much wider than the actual range obtained during a surgery of an individual patient. During a surgery, for example, the same parameter is then measured and a histogram distribution is created using the same parameter value bins. This distribution for the individual patient may contain a fixed number of values, e.g. 300, and the distribution may be updated using the full adaptation method described above. It is also possible that a cumulative distribution of the parameter values of the individual patient is collected and that the so obtained distribution counts are scaled down to a predetermined match in total counts to the patient group distribution. In such a case, the individual patient distribution may represent the parameter values since the beginning of the surgery till the current moment during surgery. An example of a normalized patient-specific distribution curve 92 obtained during a surgery is presented in FIG. 9b.

The normalized patient-specific distribution is then added in a predetermined proportion to the normalized patient group distribution, and an average total distribution curve 93 is formed, as shown in FIG. 9c. In this example, the two normalized distributions are weighted equally in the total distribution. For calculating the input parameter value array for the partially adapted histogram transformation a cumulative sum of the average total distribution is then constructed as shown in FIG. 9d. If the histogram transformation arrays are 101 element long, for example, the new values for the input bins of the histogram transformation can be obtained by projecting the cumulative sum values 0, 1, 2, . . . , 100 of the Y-axis to the parameter value axis (X-axis), as is shown by dashed lines in FIG. 9d. The X-axis values obtained in this way form the input values of the input array for the histogram transformation. The actual histogram transformation is then executed without adaptation. In this embodiment, input values for the input array are thus obtained by adding a group distribution curve to the patient-specific distribution curve and then defining the input values for the input array by means of the cumulative distribution function of the summed distribution curve. Once being defined in the above-described manner, the input values of the input array remain fixed for a predetermined update interval, which can typically represent about 100 new individual parameter values.

The proportions of the adaptive and non-adaptive values in the combined input may vary. The same applies to the size of the steps between consecutive (fixed) values stored in the input or output arrays. For example, in the example presented in connection with FIGS. 9a to 9d each consecutive input array bin contained one percent of the input values. However, the steps may also be such that a certain other percentage of values is within each step (i.e. in each bin), in which case the step may be smaller around one range of the input values and correspondingly larger around another range of the input values.

Partial adaptation to the incoming signal may also be accomplished so that only every $i^{th}$ (i=2, 3, 4 . . . ) new data point obtained from the pre-processing phase replaces the oldest value in the input array. In this way, the input array values originate from further in the past. The update procedure chosen thus controls the length of the memory for the adaptation to the signal.

Figure 10:
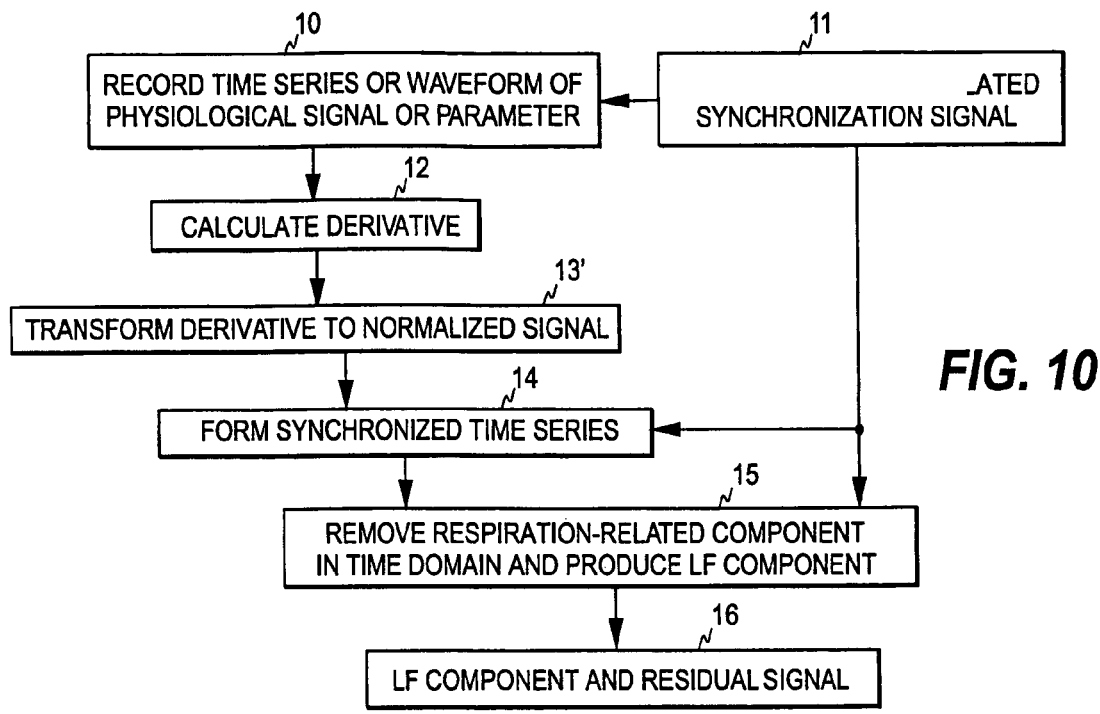
FIG. 10 is a flow diagram illustrating a further embodiment of the invention.

The derivation and the normalization may also be used together. FIG. 10 illustrates a combinatory embodiment of the invention, in which both the derivative of the measurement signal and the normalization are used. In this embodiment, the derivative of the measurement signal is thus normalized at step 13', and the signal so obtained is subjected to the interpolation step 14 to synchronize it with the respiration rhythm. The other steps of the method are performed as described above.

All the embodiments discussed in connection with FIGS. 1 to 5 may also be used when normalization is utilized. However, the embodiments in which the residual signal is further divided into frequency components is not needed in connection with the normalization, since the LF component is also indicative of the HF component (since their total power is constant).

In the present invention, a signal indicative of the irregularity of the respiration modulation in the physiological signal is thus formed based on a signal indicative of the respiration rhythm of the patient. The former signal is then used to obtain an estimate of the state of the ANS of the patient. The irregularity of the respiration modulation appears in the LF or HF components, or in the above irregular signal component obtained based on the entire signal or the residual signal. These components may then be used to calculate the sympatho-vagal balance indicative of the state of the ANS. The irregularity of the respiration modulation also appears in the correlation or variance calculated. The correlation and the variance may be used directly as indicators of the state of the ANS, although they may also be used to calculate other variables, such as an index indicative of the adequacy of analgesia or an index indicative of the depth of anesthesia.

Figure 11:
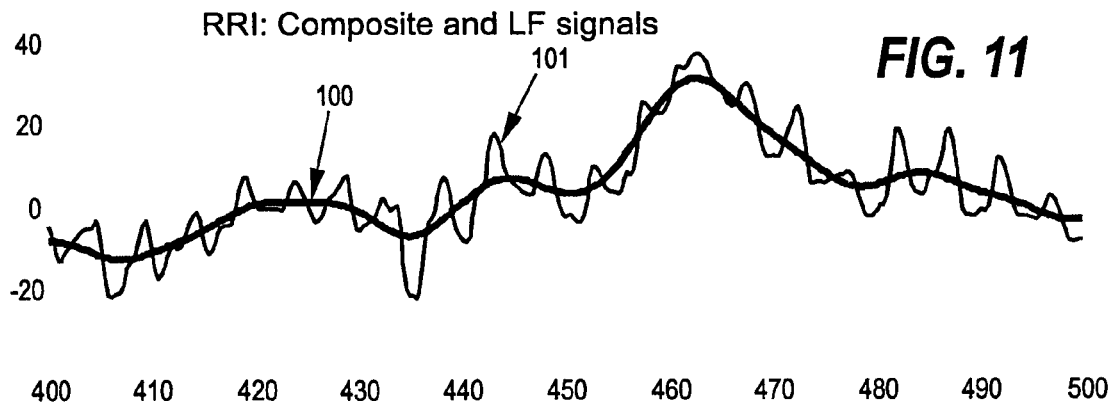
FIG. 11 illustrates an RRI signal and its low frequency component extracted by the method of the invention.
Figure 12:
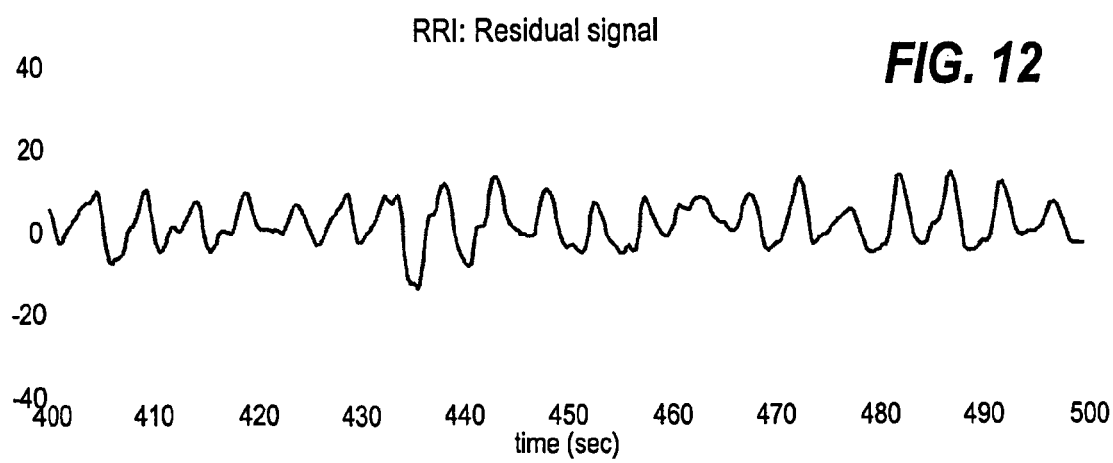
FIG. 12 illustrates the residual signal remaining after the low frequency component has been extracted from the RRI signal of FIG. 10.

FIGS. 11 and 12 illustrate the results obtained using the embodiment discussed in connection with FIGS. 2 and 3. FIG. 11 illustrates an RRI signal 101 obtained from the patient and the low frequency component 100 determined in the above-mentioned manner and obtained with a delay of about one respiration cycle. FIG. 11 illustrates the (first) residual signal remaining after the low frequency component has been subtracted from the RRI signal. The residual signal comprises the respiration modulation and the B2B component.

Figure 13:
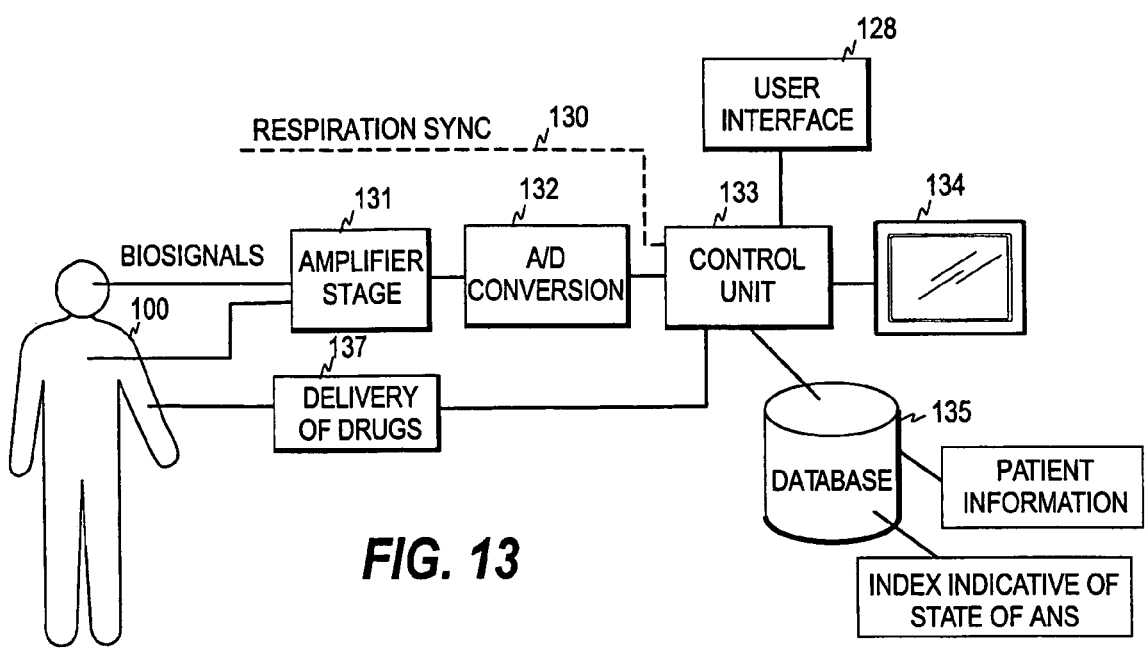
FIG. 13 illustrates one embodiment of a system according to the invention.

FIG. 13 illustrates one embodiment of the system according to the invention. The physiological signal(s) obtained from one or more sensors attached to a patient 100 is/are supplied to an amplifier stage 131, which amplifies the signals before they are sampled and converted into digitized format in an A/D converter 132. The digitized signals are supplied to a control unit 133 (including a microprocessor), which may then record the signals.

The control unit is provided with a database or memory unit 135 holding the digitized signal data obtained from the sensor(s). Using the data, the control unit may perform the above-described pre-processing phase and form the time series forming each first measurement signal utilized. In connection with the pre-processing phase, the control unit may also retrieve patient information from the memory unit to check whether some of the physiological signals are to be omitted when forming the first measurement signal(s).

In the embodiment of FIG. 13, the control unit further receives the second measurement signal 130 indicative of the respiration cycle of the patient, forms the respiration-locked time series of each physiological signal, and generates the indicator signal(s) characterizing respiration modulation in the physiological signal. As discussed above, the indicator signal may then be used in various ways to obtain an indication of the state of the ANS of the patient. This indication may be generated by the control unit or it may be calculated elsewhere in the network using the indicator signal(s) calculated by the control unit.

Although one control unit (processor) may perform the calculations needed, the processing of the data may also be distributed among different processors (servers) within a network, such as a hospital LAN (local area network).

The control unit may display the results on the screen of a monitor 134 connected to the control unit, and it may further supply the calculated index/indicator as input data to a device or system 137 delivering drugs, such as analgetics, to the patient, which enables automatic control of the patient's level of antinociception, for example. The system further includes user interface means 138 through which the user may control the operation of the system.

Although the invention was described above with reference to the examples shown in the appended drawings, it is obvious that the invention is not limited to these, but may be modified by those skilled in the art without departing from the scope and spirit of the invention.

The invention claimed is:

1. A method for monitoring the state of the autonomous nervous system of a patient, the method comprising the steps of:
    acquiring a first measurement signal from a patient, the first measurement signal representing a physiological signal measured from the patient;
    obtaining a second measurement signal in the time domain indicative of a respiration rhythm of the patient;
    deriving, based on the second measurement signal, at least one respiration-locked time series of the first measurement signal, the respiration-locked time series being locked to the respiration rhythm of the patient;
    utilizing the at least one respiration-locked time series to generate at least one measurement signal indicative of irregularity of respiration modulation in the first measurement signal; and
    employing the third measurement signal for obtaining an indication of the state of the autonomous nervous system of the patient.

2. A method according to claim 1, wherein the generating step includes dividing the first measurement signal into a low frequency component and a residual signal.

3. A method according to claim 2, wherein the obtaining step includes obtaining the second measurement signal, the second measurement signal indicating the respiration rate of the patient.

4. A method according to claim 2, wherein the generating step further includes dividing the residual signal into a regular signal component and an irregular signal component, wherein the regular signal component remains substantially constant from one respiration cycle to another and the irregular signal component varies from one respiration cycle to another.

5. A method according to claim 2, wherein the generating step further includes a sub-step of dividing the residual signal into a high frequency component and to a beat-to-beat component caused by beat-to-beat variations in the physiological signal.

6. A method according to claim 2, further comprising a step of filtering the residual signal to obtain a high frequency component of the first measurement signal.

7. A method according to claim 1 wherein the generating step includes deriving a difference time series, the difference time series including a predetermined number of difference values for each respiration cycle of the patient, each difference value representing the difference of two signal values which are one respiration cycle apart in the respiration-locked time series of the first measurement signal.

8. A method according to claim 7, wherein the generating step includes a step of defining a low frequency component of the first measurement signal based on the difference time series, the low frequency component serving as the at least one indicator signal.

9. A method according to claim 7, wherein the generating step further includes calculating a variance for a predetermined number of difference values.

10. A method according to claim 1, wherein the generating step includes calculating a correlation value between a first and second instance of the respiration-locked time series of the first measurement signal, wherein the first instance includes L latest signal values in the first measurement signal and the second instance includes L latest signal values in the first measurement signal delayed by an integer number of respiration cycles.

11. A method for monitoring the state of the autonomous nervous system of a patient, the method comprising the steps of:

acquiring a first measurement signal from a patient, the first measurement signal representing a physiological signal measured from the patient;

obtaining a second measurement signal indicative of a respiration rhythm of the patient; and generating, based on the first and second measurement signals, at least one indicator signal for obtaining an indication of the state of the autonomous nervous system of the patient, wherein the generating step includes deriving, based on the second measurement signal, at least one respiration-locked time series of the first measurement signal, the respiration-locked time series being locked to the respiration rhythm of the patient, the difference time series including a predetermined number of difference values for each respiration cycle of the patient, each difference value representing the difference of two signal values that are one respiration cycle apart in the respiration-locked time series of the first measurement signal, wherein the generating step further includes a step of defining a low frequency component of the first measurement signal based on the difference time series, the low frequency component serving as the at least one indicator signal, wherein the defining step further includes summing the difference values, thereby forming a time series representing the low frequency component of the first measurement signal.

12. A method for monitoring the state of the autonomous nervous system of a patient, the method comprising the steps of:

acquiring a first measurement signal from a patient, the first measurement signal representing a physiological signal measured from the patient;

obtaining a second measurement signal indicative of a respiration rhythm of the patient; and generating, based on the first and second measurement signals, at least one indicator signal for obtaining an indication of the state of the autonomous nervous system of the patient, wherein the generating step includes deriving, based on the second measurement signal, at least one respiration-locked time series of the first measurement signal, the respiration-locked time series being locked to the respiration rhythm of the patient, the difference time series including a predetermined number of difference values for each respiration cycle of the patient, each difference value representing the difference of two signal values that are one respiration cycle apart in the respiration-locked time series of the first measurement signal, wherein the generating step further includes a step of defining a low frequency component of the first measurement signal based on the difference time series, the low frequency component serving as the at least one indicator signal, wherein the defining step includes:

filtering the difference values to form a time series of filtered difference values; and summing the filtered difference values, thereby forming a time series representing the low frequency component of the first measurement signal.

13. A method according to claim 1, wherein the acquiring step includes the steps of:

measuring the physiological signal from the patient; and calculating a time derivated signal of the physiological signal, the time derivated signal being the first measurement signal.

14. A method according to claim 1, wherein the acquiring step includes the steps of:

measuring the physiological signal from the patient; and calculating a normalized signal of the physiological signal, the normalized signal being the first measurement signal.

15. A method according to claim 1, wherein in the acquiring step includes the steps of:

measuring the physiological signal from the patient;

calculating a time derivated signal of the physiological signal; and calculating a normalized signal of the time derivated signal, the normalized signal being the first measurement signal.

16. A method according to claim 1 wherein the generating step includes forming the residual signal by subtracting the time series representing the low frequency component from the respiration-locked time series of the first measurement signal.

17. A method according to claim 1, further comprising a step of determining, based on the at least one indicator signal, a sympatho-vagal balance of the patient.

18. A method according to claim 1, further comprising a step of determining, based on the at least one indicator signal, a first variable representing power of sympathetical activation of the autonomous nervous system and a second variable representing power of a signal component representing regular respiration modulation in the first measurement signal.

19. A method according to claim 1, further comprising a step of determining, based on the at least one indicator signal, an index indicative of adequacy of analgesia.

20. A method according to claim 1, further comprising a step of determining, based on the at least one indicator signal, an index indicative of depth of anesthesia.

21. A method according to claim 1, wherein the obtaining step includes obtaining the second measurement signal from a respirator.

22. A method according to claim 1, wherein the obtaining step includes obtaining the second measurement signal from a transducer attached to the patient.

23. A method according to claim 1, wherein deriving step comprises deriving the at least one respiration-locked time series, in which the at least one respiration-locked time series includes a predetermined number of signal values for each respiration cycle of the patient and information about the respiration rhythm of the patient.

24. An arrangement for monitoring the state of the autonomous nervous system of a patient, the arrangement comprising:

first means for acquiring a first measurement signal from a patient, the first measurement signal representing a physiological signal measured from the patient;

second means for obtaining a second measurement signal in the time domain indicative of a respiration rhythm of the patient;

third means operable to derive, based on the second measurement signal, at least one respiration-locked time series of the first measurement signal, the respiration-locked time series being locked to the respiration rhythm of the patient, wherein the third means generates a third measurement signal based on the at least one respiration-locked time series indicative of irregularity of respiration modulation in the first measurement signal; and fourth means for employing the third measurement signal to obtain an indication of the state of the autonomous nervous system of the patient.

25. An arrangement according to claim 24, wherein the third means are configured to derive a difference time series, the difference time series including a predetermined number of difference values for each respiration cycle, each difference value representing the difference of two signal values, which are one respiration cycle apart in the respiration-locked time series of the first measurement signal.

26. An arrangement according to claim 25, wherein the third means are further configured to calculate a variance value based on a predetermined number of difference values.

27. An arrangement according to claim 24, wherein the third means are configured to calculate a correlation value between a first and second instance of the respiration-locked time series of the first measurement signal, wherein the first instance includes L latest signal values in the first measurement signal and the second instance includes L latest signal values in the first measurement signal delayed by one respiration cycle.

28. An arrangement according to claim 24, further comprising means for calculating a sympatho-vagal balance based on the at least one indicator signal.

29. An arrangement for monitoring the state of the autonomous nervous system of a patient, the arrangement comprising:
    first means for acquiring a first measurement signal from a patient, the first measurement signal representing a physiological signal measured from the patient;
    second means for obtaining a second measurement signal indicative of a respiration rhythm of the patient;
    third means for generating, by means of the first and second measurement signals, at least one indicator signal for obtaining an indication of the state of the autonomous nervous system of the patient; and
    a fourth means for deriving, based on the second measurement signal, at least one respiration-locked time series for the first measurement signal, the respiration-locked time series being locked to the respiration rhythm of the patient,
    wherein the third means is configured to derive a difference time series, the difference time series including a predetermined number of difference values for each respiration cycle, each difference value representing the difference of two signal values, which are one respiration cycle apart in the respiration-locked time series of the first measurement signal,
    wherein the third means are further configured to filter the difference values for obtaining filtered difference values, to form a time series of the filtered difference values, and to sum the filtered difference values.

* * * * *